United States Patent
Thompson et al.

(10) Patent No.: US 7,655,188 B2
(45) Date of Patent: Feb. 2, 2010

(54) ASSEMBLY FOR COLLECTING SAMPLES FOR PURPOSES OF IDENTIFICATION OR ANALYSIS AND METHOD OF USE

(75) Inventors: Cyril V. Thompson, Knoxville, TN (US); Rob R. Smith, Knoxville, TN (US)

(73) Assignee: UT-Battelle, LLC, Oak Ridge, TN (US)

( * ) Notice: Subject to any disclaimer, the term of this patent is extended or adjusted under 35 U.S.C. 154(b) by 1062 days.

(21) Appl. No.: 11/194,095

(22) Filed: Jul. 29, 2005

(65) Prior Publication Data

US 2007/0025881 A1    Feb. 1, 2007

(51) Int. Cl.
 *B01L 3/00* (2006.01)
(52) U.S. Cl. .......................... 422/100; 436/180; 604/1; 604/2; 604/3; 250/288
(58) Field of Classification Search ................ 422/68.1, 422/88, 99–102; 250/288; 435/287.7; 604/1–3; 436/180
See application file for complete search history.

(56) References Cited

U.S. PATENT DOCUMENTS

| | | | | |
|---|---|---|---|---|
| 33,234 A | * | 9/1861 | Boardman | 604/1 |
| 982,232 A | * | 1/1911 | Bartholomew | 604/1 |
| 1,256,831 A | * | 2/1918 | Rogers | 604/1 |
| 1,652,108 A | * | 12/1927 | Tietjen | 604/1 |
| 1,711,352 A | * | 4/1929 | Jeffreys | 606/106 |
| 1,858,694 A | * | 5/1932 | Walsh | 604/11 |
| 1,908,403 A | * | 5/1933 | Budde | 604/1 |
| 4,364,760 A | * | 12/1982 | Higuchi et al. | 55/523 |
| 4,401,130 A | * | 8/1983 | Halford et al. | 15/208 |
| 4,718,889 A | * | 1/1988 | Blasius et al. | 604/1 |
| 5,766,143 A | * | 6/1998 | Bennett | 604/1 |
| 5,780,305 A | * | 7/1998 | Chisum | 436/174 |
| 5,874,045 A | * | 2/1999 | Chisum | 422/58 |
| 6,541,419 B2 | * | 4/2003 | Shore et al. | 502/400 |
| 2004/0181170 A1 | * | 9/2004 | Wallach | 600/569 |
| 2005/0076461 A1 | * | 4/2005 | Tsaur | 15/209.1 |

* cited by examiner

*Primary Examiner*—Brian R Gordon
*Assistant Examiner*—Shogo Sasaki
(74) *Attorney, Agent, or Firm*—Michael E. McKee (57) ABSTRACT

An assembly and an associated method for collecting a sample of material desired to be characterized with diagnostic equipment includes or utilizes an elongated member having a proximal end with which the assembly is manipulated by a user and a distal end. In addition, a collection tip which is capable of being placed into contact with the material to be characterized is supported upon the distal end. The collection tip includes a body of chemically-inert porous material for binding a sample of material when the tip is placed into contact with the material and thereby holds the sample of material for subsequent introduction to the diagnostic equipment.

12 Claims, 5 Drawing Sheets

ASSEMBLY FOR COLLECTING SAMPLES FOR PURPOSES OF IDENTIFICATION OR ANALYSIS AND METHOD OF USE

This invention was made with Government support under Contract No. DE-AC05-00OR22725 awarded by the U.S. Department of Energy to UT-Battelle, LLC, and the Government has certain rights to the invention.

BACKGROUND OF THE INVENTION

This invention relates generally to the obtaining of samples for purposes of identification or analysis and relates, more particularly, to a means for collecting such a sample from a source.

The class of equipment with which this invention is utilized includes diagnostic equipment, such as a mass spectrometer, used for characterizing (e.g. identifying or analyzing) materials. It is not uncommon, for example, that military or rescue personnel occasionally come across material, such as a liquid contained in an unlabeled drum, that cannot be readily identified. Due to the chances that such material may be harmful or toxic to humans, it is important that the material be correctly identified or characterized before it is handled. For purposes of identifying the material as quickly as possible, the diagnostic equipment to be employed, such as a mass spectrometer, is commonly mounted upon a mobile unit and driven to the site where a material which is desired to be identified is located.

There is normally associated with such diagnostic equipment a probe to which a sample amount of the material to be identified is introduced to the equipment. The diagnostic equipment of the class with which this invention is concerned is normally adapted to analyze and identify materials when in the vapor state. Therefore, there is typically associated with the probe a heater so that when a liquid sample of the material to be identified is placed adjacent the probe, the heater vaporizes (at least some of) the liquid sample, and the vaporized sample is, in turn, conducted to the diagnostic equipment for identification or analysis.

Heretofore, an amount of the material to be identified or analyzed has first been collected upon the surface of a wheel having a rubber-like periphery, and the surface of the wheel, with an amount of material clinging thereto, is thereafter placed into engagement with the probe. In this connection, the periphery of the wheel is initially moved (e.g. rolled) across or dipped within the material to be identified or analyzed so that an amount of the material adheres to the peripheral surface of the wheel. The surface of the wheel is then pressed into engagement with the probe so that a sample amount of material which clings to the peripheral surface of the wheel is transferred from the wheel surface to the probe.

Such a prior art technique of transferring an amount of material from a source to the diagnostic equipment is limited in that volatile compounds (which may comprise the material to be analyzed) can dissipate very quickly from the wheel surface so that very little sample is ultimately transferred from the wheel surface to the diagnostic equipment (e.g. a mass spectrometer); and if the amount of sample which is conducted from the wheel surface to the diagnostic equipment is too small, then the signal which is generated by a signal-generating means of the diagnostic equipment from the sample might not be strong enough to accurately identify or characterize the material. By comparison and in the case of materials which are comprised of less volatile compounds, too much material could be transferred from the wheel surface to the diagnostic equipment and ultimately degrade the signal-generating means of the equipment.

It would be desirable to provide an improved means for collecting an amount of sample material from a source and for transferring the collected sample to a probe associated with diagnostic equipment for purposes of identifying or analyzing the sample.

Accordingly, it is an object of the present invention to provide a new and improved means and method for collecting a sample from a source of material to be identified or analyzed and transferring the collected sample to the probe associated with diagnostic equipment of the aforedescribed class.

Another object of the present invention is to provide such a collection means whose use is less likely to effect the transfer of either too much or too little an amount of the sample to the diagnostic equipment for identification or analysis.

Still another object of the present invention is to provide such a collection means which is well-suited for collecting a sample amount of material, whether the material is relatively volatile or not very volatile.

Yet another object of the present invention is to provide such a collection means which is highly sensitive to the sample being collected, contributes to a more accurate identification or characterization of the sample, is relatively easy to use, provides greater safety for the operator, and is less expensive to use than is the wheel of the prior art technique described above.

A further object of the present invention is to provide such a collection means which is uncomplicated in structure, yet effective in operation.

SUMMARY OF THE INVENTION

This invention resides in an assembly for collecting a sample of material desired to be characterized with diagnostic equipment including a probe through which an amount of the sample is introduced to the diagnostic equipment and a method of transferring a sample of the material to the probe.

The assembly of the invention includes an elongated member having a proximal end with which the assembly is manipulated by a user and a distal end. In addition, a collection tip is supported upon the distal end and which can be placed into engagement with material from which a sample is desired to be taken. The collection tip includes a body of chemically-inert porous material for binding a sample of material when the tip is placed into contact with the material for subsequent introduction of an amount of the bound sample through the probe of the diagnostic equipment.

In one embodiment of the assembly, the assembly includes a cup section which is disposed about the elongated member so that the opening of the cup section is directed opposite the proximal end of the member and which is positionable about the collection tip of the assembly when the tip is placed adjacent the probe for transfer of an amount of the collected sample to the diagnostic equipment. By enclosing the airspace surrounding the collected sample as the sample is exposed to the probe, the cup section helps to focus, or direct, the collected sample upon the probe so that neither too much nor too little sample is ultimately transferred from the collection tip to the diagnostic equipment. Further still, the cup section increases the duration of the sample signal capable of being generated by the diagnostic equipment thereby allowing a fuller characterization of the sample by the diagnostic equipment.

The method of the invention includes steps involved in using the assembly of the invention. In particular, the method includes the steps of placing the collection tip into contact with the material desired to be characterized so that the collection tip wicks, and thereby holds, a sample of material and then placing the collection tip adjacent the probe of the diagnostic equipment for introduction of an amount of the bound sample to the diagnostic equipment.

DETAILED DESCRIPTION OF ILLUSTRATIVE EMBODIMENTS

Figure 1:
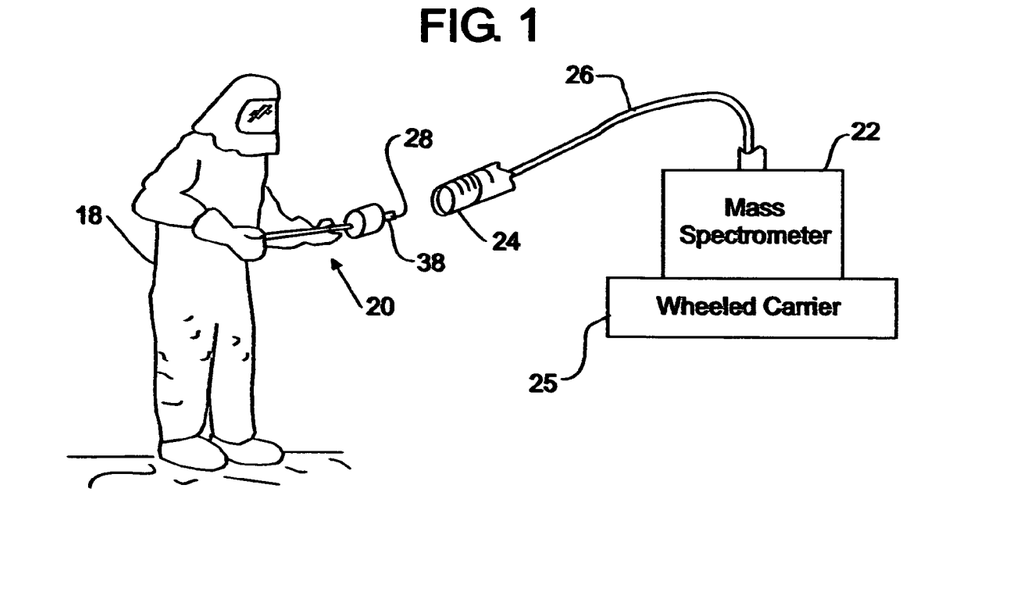
FIG. 1 is a perspective view of a sample collection assembly within which features of the present invention are embodied and shown being utilized in a schematically-represented environment of intended use.

Turning now to the drawings in greater detail and considering first FIG. 1, there is illustrated an embodiment, generally indicated 20, of a collection assembly shown utilized with diagnostic equipment in an exemplary environment of intended use. In particular, the diagnostic equipment of the FIG. 1 environment includes a mass spectrometer 22 with which a sample 28 of material is to be identified or analyzed, a probe 24 which is associated with the mass spectrometer 22 and through which an amount of the sample 28 is introduced to the mass spectrometer 22, and a capillary tube 26 which is joined to so as to extend between the probe 24 and the mass spectrometer 22. During use of the FIG. 1 equipment, a sample of material desired to be identified or analyzed is placed adjacent the probe 24, and a pump (not shown) mounted internally of the mass spectrometer 22 draws an amount of the sample 28 (in a vaporized state) in sequence through the probe 24 and then through the capillary tube 26 to the mass spectrometer 22 where an analysis is performed upon the sample (e.g. for the purpose of identifying or characterizing the material of the sample 28). To facilitate movement of the mass spectrometer 22 to a site where an analysis of the sample 28 is desired to be performed, the mass spectrometer 22 is commonly mounted upon a wheeled carrier 25 (e.g. a mobile unit, such as a truck).

Samples which are commonly analyzed with the FIG. 1 equipment are in a liquid state when collected, while the mass spectrometer 22 is normally adapted to perform its analysis upon a sample when the sample is in a vaporized state. Therefore and for purposes of vaporizing an amount of the sample 28 when the sample 28 is placed adjacent the probe 24, there is associated with the probe 24 an internal heater (not shown) which is capable of heating the amount of the sample 28 which is positioned adjacent the probe 24 to a relatively high temperature (e.g. about 180° C.), and the capillary tube 26 is, in turn, heated by a resistance heating element (not shown) which extends along the length of the capillary tube 26 to ensure that the amount of the sample 28 which is drawn into the capillary tube 26 is maintained in a vaporized state as it is conducted from the probe 24 to the mass spectrometer 22.

As will be apparent herein, the collection assembly 20 is used to collect a sample 28 of material to be identified or analyzed and to transfer an amount of the sample 28 from the site of collection to the probe 24. In other words, rather than move and manipulate the probe 24 into contact with an amount of material to be analyzed, the collection assembly 20 is used to manually transfer a sample amount of material to be analyzed from one site (e.g. the material source, such as an unlabeled drum) to a position adjacent the probe 24. Accordingly, the collection assembly 20 is adapted to be held and manipulated with the hands of an operator 18 during the steps of collecting the sample 28 and transferring the sample 28 to the probe 24.

Figure 2:
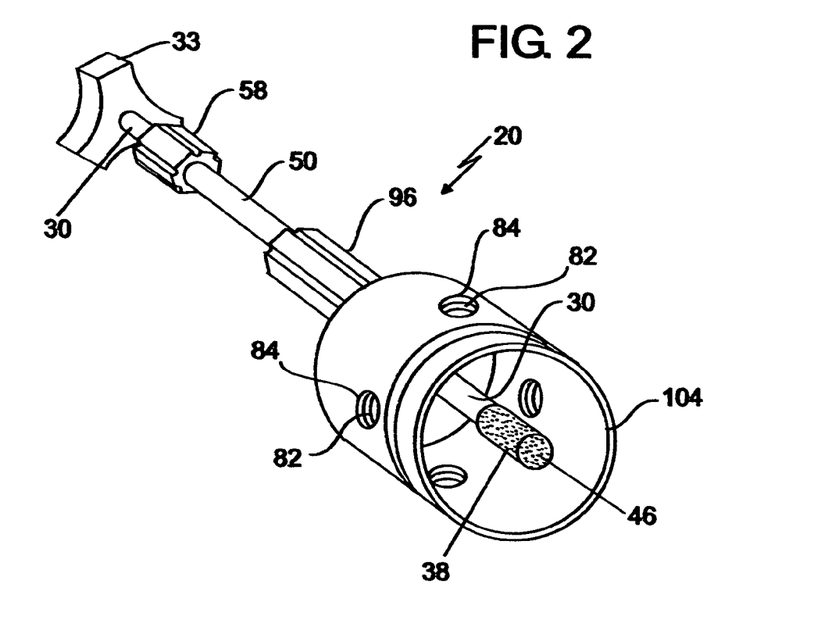
FIG. 2 is a perspective view of the FIG. 1 embodiment.
Figure 3:
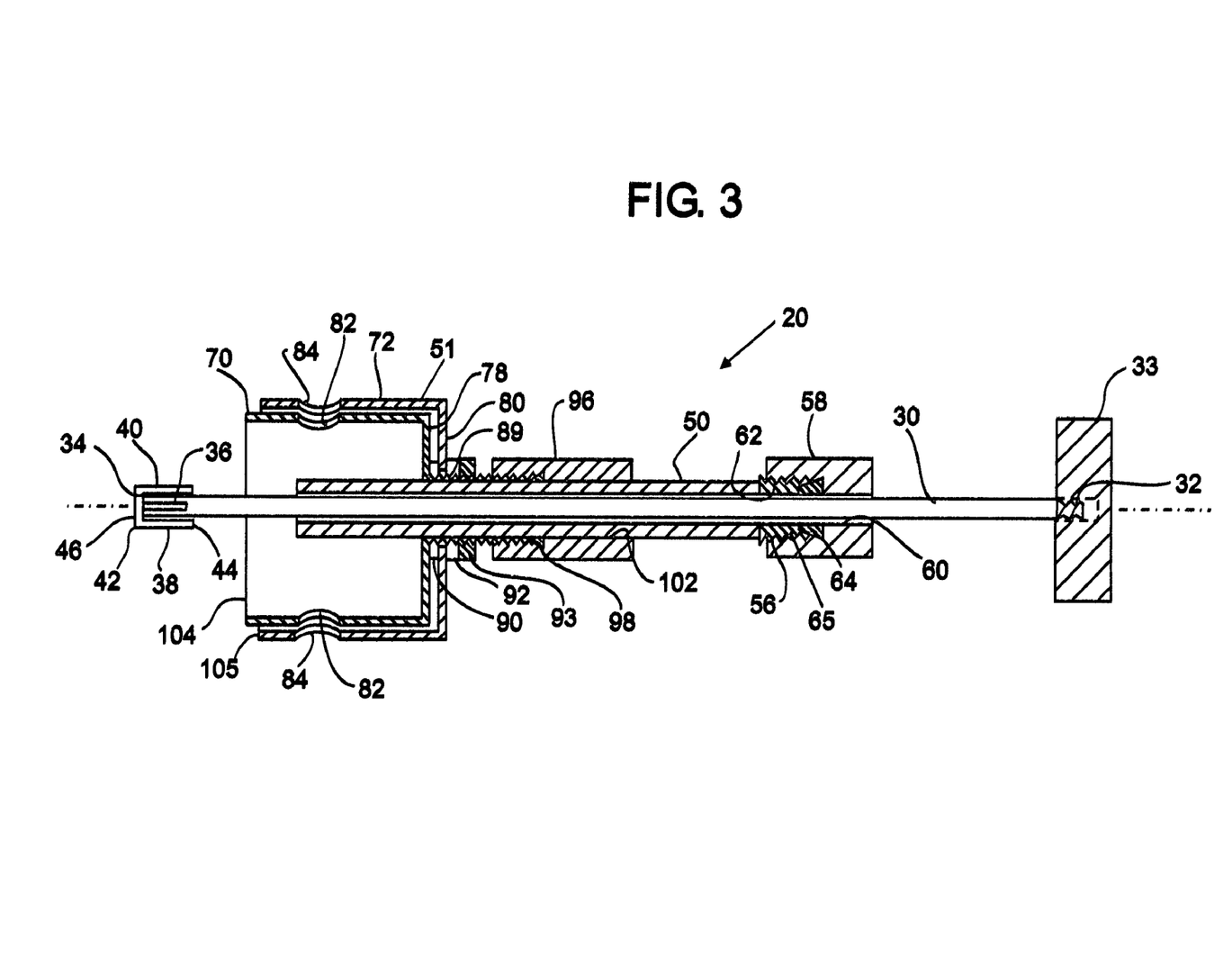
FIG. 3 is a longitudinal cross-sectional view of the FIG. 1 embodiment.
Figure 4:
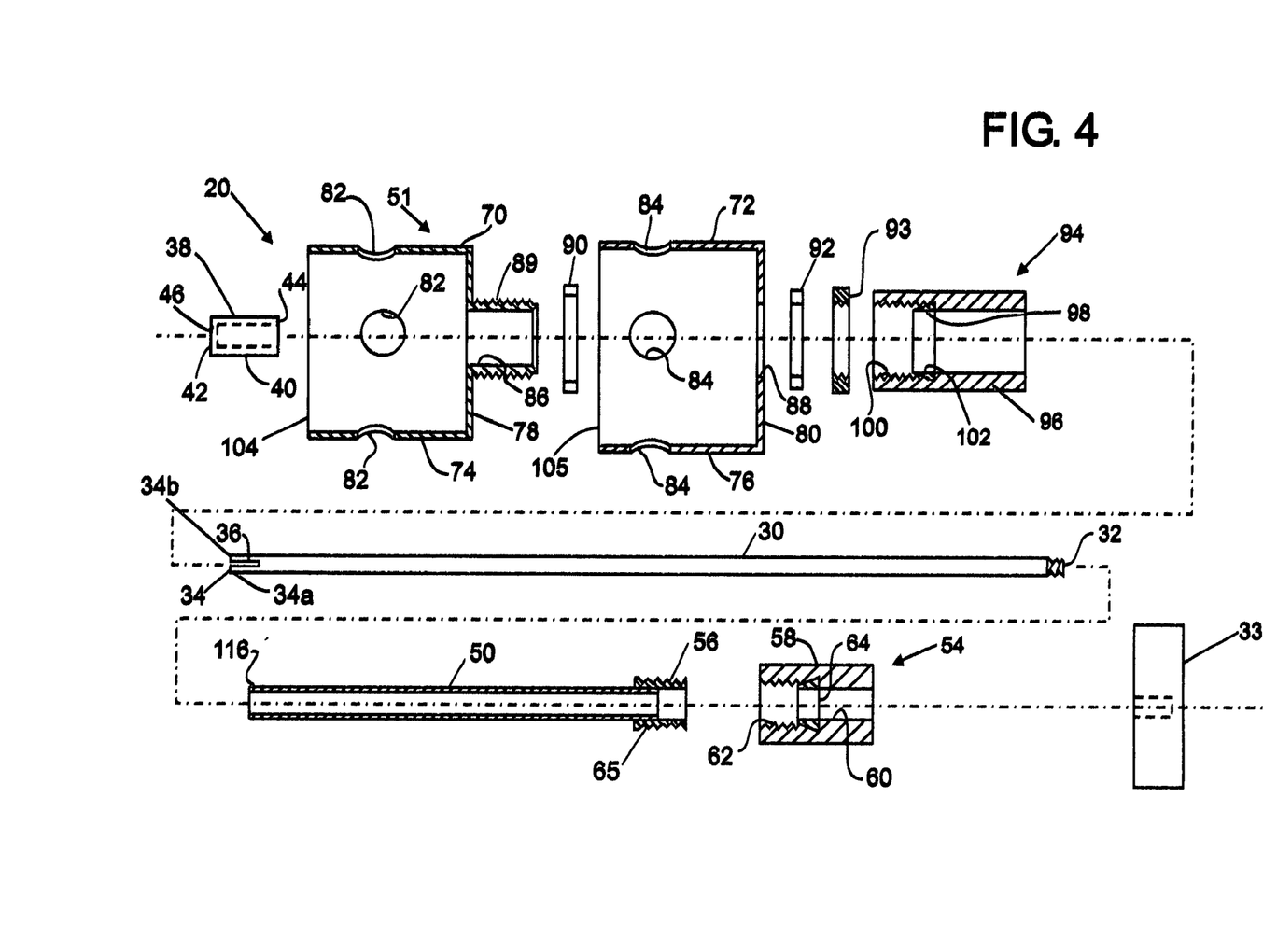
FIG. 4 is a view similar to that of FIG. 3, shown exploded.

With reference to FIGS. 2-4, the collection assembly 20 includes a main, elongated member in the form of an elongated rod 30 having a proximal end 32 with which the assembly 20 can be held by the operator 18 (FIG. 1) and a distal end 34 which is capable of being manually guided into contact with an amount of material to be analyzed. The elongated rod 30 of the depicted assembly 20 is cylindrical in form, has a diameter which is about 0.25 inches, and has a length which is about 14.0 inches. To enhance the capacity of the proximal end 32 of the rod 30 to be grasped by an operator, a handle 33 can be threadably secured upon the proximal end 32 of the rod 30. In addition and for a purpose which will become apparent herein, a portion of the rod 30 adjacent the distal end 34 thereof has a slit 36 which is formed (e.g. cut) therein so as to open out of the distal end 34 and extend therealong for a relatively short distance (e.g. about 0.7 inches).

It is a feature of the assembly 20 that it includes a collection tip 38 of chemically-inert porous material which is capable of being held upon the distal end 34 of the rod 30 during a sample collecting operation. The tip 38 possesses a sufficient inertness so that it does not affect or contribute to the characterization of the sample being tested by the diagnostic equipment 22. In other words, the material of the tip 38 is inert with respect to the material of the sample being collected and is inert with respect to the diagnostic equipment to perform the analysis upon the material of the sample. Still further, the porous nature of the material of the tip 38 which, by virtue of its porosity, defines a plurality of voids disposed across and throughout its surfaces. As will be apparent herein, these voids serve to wick an amount of sample 28 from material to be analyzed for collection by the assembly 20 and, when subsequently placed adjacent a probe 24 for introduction thereto, advantageously releases the sample bound thereto over a period of time, rather than all at once.

Within the depicted assembly 20, the tip 38 is shaped so as to be snugly positioned about the distal end 34 of the assembly 20 so that during the sample-collecting and transferring processes, the tip 38 remains held about the distal end 34 of the rod 30. To this end and as best shown in FIG. 4, the collection tip 38 is cup-shaped in form having substantially cylindrically-shaped walls 40 and two opposite ends 42, 44 and an end portion 46 which spans the cylindrically-shaped wall 40 so as to close one end 42 of the tip 38. The other, or open, end 44 of the tip 38 is sized to be accepted by the distal end 34 of the rod 30 and remain thereabout during a sampling operation.

In order for the tip 38 to fit snugly about the distal end 34 of the depicted assembly 20, the internal diameter of the collection tip 38 preferably measures 0.25 inches ±0.003 inches. Other exemplary dimensions of the tip 38 are as follows: The length of the tip 38 can be about 1.000 inches, the outer diameter of the tip 38 can be about 0.379 inches, the thickness of the cylindrically-shaped walls 40 of the tip 38 can be about 0.065 inches, and the thickness of the end portion 46 of the tip 38 can be about 0.073 inches.

The aforementioned slit 36 which is provided within the distal end 34 of the rod 30 (and which separates the distal end 34 into a pair of bifurcated sections 34a and 34b) permits a user of the collection assembly 20 to slightly adjust the outer diameter of the distal end 34 if, for example, the internal diameter of a collection tip 38 which is desired to be directed open-end-first upon the distal end 34 of the rod 30 is discovered to be either too small to be positioned upon the distal end or too large to be snugly retained upon the distal end 34. To this end and if the inner diameter of the collection tip 38 is discovered to be too small, a user can pinch the bifurcated sections 34a and 34b of the distal end 34 closer together until the collection tip 38 can be directed endwise, and thereby fitted onto, the distal end 34. By comparison, if the inner diameter of the collection tip 38 is discovered to be too large, the bifurcated sections 34a and 34b of the distal end 34 can be slightly spread apart with an appropriate tool, such as a slotted screwdriver, until the collection tip 38 fits snugly thereabout when directed endwise over the distal end 34. Accordingly, the slit 36 allows the outer diameter of the distal end 34 to be altered to enable collection tips of slightly varied internal diameters to be snugly accepted by the distal end 34 and is advantageous in this respect.

Because the collection tip 38 is comprised of a porous material (e.g. stainless steel), the material (which is commonly in a liquid state) into which the distal end 34 of the rod 30 is placed into contact is wicked onto and throughout the surfaces of the tip 38 and is bound thereon and therein (i.e. by capillary diffusion) until transferred from the tip 38 to the probe 24 (FIG. 1) for analysis. Thus, the collection tip 38 provides a means for acquiring a sample of material and holding, or binding, the sample until transferred from the tip 38 to the probe 24. The material out of which the collection tip 38 of porous material is constructed is preferably adapted to resist degradation or corrosion when placed into contact with the material to be sampled to reduce any likelihood that the identification of characterization of the material of the sample 28 by the mass spectrometer 22 will be adversely influenced by corrosion or degradation of the tip 38. For this purpose and due to its resistance to the corrosive effects of highly corrosive substances, such as sulfuric acid, stainless steel has been found to be sell-suited for use as the porous material of the collection tip 38. However, other materials, such as materials available under and known by the trade designation MONEL, HASTELLOY OR INCONEL or ceramics, can be used. Collection tips 38 comprised of porous stainless steel are currently available from Applied Porous Technologies, Inc. of Tariffville, Conn.

With reference still to FIGS. 2-4, the assembly 20 further includes an elongated outer tube 50 which is positioned about the rod 30 and which extends for a substantial distance therealong and a cup-shaped enclosure assembly 51 which is positioned about the outer tube 50. The outer tube 50 is positioned about the rod 30 to accommodate a sliding movement of the tube 50 relative to and along the length of the rod 30, and the enclosure assembly 51 is slidably positioned about the tube 50 to accommodate a sliding movement of the enclosure assembly 51 relative to and along the length of the tube 50. As will be apparent herein, the capacity of the tube 50 to slidably move relative to and along the length of the rod 30 permits an adjustment in position of the tube 50 along the length of the rod 30, and the capacity of the enclosure assembly 51 to slidably move relative to and along the length of the tube 50 permits an adjustment in position of the enclosure assembly 51 along the length of the tube 50.

The outer tube 50 is sized so as to be closely accepted by the elongated rod 30 and still permit sliding movement of the tube 50 relative to and along the length of the rod 30. In the depicted assembly 20, the tube 50 has an inner diameter of about 0.275 inches, an outer diameter of about 0.375 inches and a length of about 9.0 inches.

It is a feature of the assembly 20 that it includes means, generally indicated 54, for releasably securing the outer tube 50 in a stationary position along the length of the elongated rod 30. In this connection, the end of the tube 50 corresponding with the proximal end 32 of the rod 30 has an externally-threaded union 65 swaged thereabout, and the means 54 for releasably securing includes a cylindrically-shaped body 58 having a central through-opening 60 which is positioned about the rod 30 for sliding movement therealong. In addition, the central through-opening 60 has a portion adjacent the end, indicated 62, thereof which is internally threaded for threadably accepting the externally-threaded union 65 positioned about the tube 50, and a resilient ferrule 64 (comprised, for example, of Teflon® or Nylon®) is snugly accepted by the through-opening 60 adjacent the internally-threaded end 62 thereof.

By positioning the internally-threaded end 62 of the body through-opening 58 into registry with the externally-threaded union 65 and then rotating the body 58 so that the internally-threaded end 62 is threaded about the externally-threaded union 65, the externally-threaded union 65 is urged against the ferrule 64 in a manner which compresses the (leading) edges of the ferrule 64 inwardly against the outer surface of the rod 30. By threadably tightening the cylindrically-shaped body 58 far enough onto the union 65, the ferrule 64 is compressed about the rod 30 so that the tube 50 is fixed in position along the length of the rod 30.

It follows from the foregoing that as long as the cylindrically-shaped body 58 is not tightly threaded about the externally-threaded union 65, the tube 50, as well as the cylindrically-shaped body 58, is free to be slidably moved along the length of the rod 30. However, when it is desired that the tube 50 be secured in a stationary condition along the length of the rod 30, the cylindrically-shaped body 58 is threadably tightened about the externally-threaded union 65 so that the ferrule 64 is compressed about the rod 30.

As best shown in FIG. 4, the cup-shaped enclosure assembly 51 is comprised of an inner cup section 70 and an outer cup section 72 which are each positioned about the tube 50 which, is in turn, positioned about the rod 30 so that each of the inner and outer cup sections 70 and 72 opens in a direction along the rod 30 opposite the direction of the proximal end 32 thereof. Each of the inner and outer cup sections 70 and 72 include cylindrical sidewalls 74 or 76 and an end wall 78 or 80 which spans (and thereby closes off) the sidewalls 74 or 76 at one end thereof. In addition, each of the cylindrical sidewalls 74 or 76 includes a plurality of (e.g. four) vent openings 82 or 84 which are regularly spaced thereabout.

With reference still to FIG. 4, each end wall 78 or 80 of the inner and outer cup sections 70 and 72 includes a central bore 86 or 88, and the inner cup section 70 includes an externally-threaded boss portion 89 which is joined to the end wall 78 thereof about the central bore 86. The central bore 86 of the inner cup section 70 is sized to be loosely accepted by the tube 50 to permit sliding movement therealong, and the central bore 88 of the outer cup section 72 is sized to be accepted by the threaded boss portion 89.

As best shown in FIG. 3, the inner cup section 70 is nestingly positioned within the outer cup section 72 so that the cylindrical sidewalls 74 and 76 are concentrically-arranged and so that the vent openings 84 of the sidewalls 76 of the outer cup section 72 are positionable in registry with the vent openings 82 of the inner cup section 70.

To assemble the inner and outer cup sections 70 and 72 about the tube 50 and with reference to both FIGS. 3 and 4, the bore 86 of the inner cup section 70 is directed over the tube 50 to position the inner cup section 70 thereabout, a first resilient washer 90 is directed over the boss portion 89, then the central bore 88 of the outer cup section 72 is directed over the boss portion 89, then a second resilient washer 92 is directed over the boss portion 89, and then a retaining nut 93 is threaded about the boss portion 89 to a snug condition thereabout so that the end wall 80 of the outer cup section 72 is captured between the first and second washers 90 and 92. With the end wall 80 of the outer cup section 72 captured between the washers 90 and 92, the outer cup section 72 is permitted to be manually rotated about the boss portion 89 and relative to the inner cup section 74 so that the vent openings 84 can be selectively moved into and out of registry with the vent openings 82. Accordingly, the opposite sides of the end wall 80 of the outer cup section 72 are not so tightly squeezed between the retaining nut 93 and the end wall 78 of the inner cup section 72 that the outer cup section 72 is prevented from rotating relative to and about the inner cup section 70. The retaining nut 93 is secured in place about the boss portion 89 using a cementing compound, such as that which is currently available under the trade designation Locktite® 242.

To prevent the enclosure assembly 51 from sliding off of the distal end, indicated 116 in FIG. 4, of the tube 50 once assembled thereabout, the distal end 116 can be flared outwardly (by appropriate mechanical means) to a small extent.

It follows that the vent openings 82 and 84 of each cup section 70 or 72 are positioned about the circumference of the corresponding cup section 70 or 72 so that by rotating the outer cup section 72 relative to and about the inner cup section 70, the vent openings 84 and 82 move into and out of registry with one another. As will be apparent herein, the capacity of the vent openings 84 and 82 to be moved into and out of registry with one another permits a user of the assembly 20 to vent the interior of the inner cup section 70 to varying degrees and thereby make adjustments for the volatility of the material being sampled with assembly 20.

Exemplary dimensions of the cup sections 70 and 72 are provided herein as follows: The inner diameter of the sidewalls 74 of the inner cup section 70 is about 2.38 inches, the outer diameter of the sidewalls 74 of the cup section 70 is about 2.45 inches, the length of the sidewalls 74 of the cup section 70 is about 2.9 inches, and the vent openings 82 are centered at about 1.25 inches from the forward edge, indicated 104 in FIGS. 3 and 4, of the inner cup section 70. The inner diameter of the sidewalls 76 of the outer cup section 72 is about 2.50 inches, the outer diameter of the sidewalls 76 of the cup section 72 is about 2.57 inches, the length of the sidewalls 76 of the cup section 76 is about 2.25 inches, and the vent openings 84 are centered at about 0.5 inches from the forward edge, indicated 105 in FIGS. 3 and 4, of the outer cup section 72. In addition, the diameter of each vent opening 82 or 84 is about 0.5 inches, and the length of the boss portion 89 is about 0.875 inches.

It is also a feature of the assembly 20 that it includes means, generally indicated 94, for releasably securing the cup-shaped enclosure assembly 51 in a stationary position along the length of the tube 50. In this connection, the means 94 for releasably securing includes a cylindrically-shaped body 96 having a central through-opening 98 which is positioned about the tube 50 for sliding movement therealong. In addition, the central through-opening 98 has a portion adjacent the end, indicated 100, thereof which is internally threaded for threadably accepting the externally-threaded portion boss portion 89 of the inner cup section 70, and a resilient ferrule 102 (comprised, for example, of Teflon® or Nylon®) is snugly accepted by the through-opening 98 adjacent the internally-threaded end 100 thereof. By positioning the internally-threaded end 100 of the body through-opening 98 into registry with the externally-threaded boss portion 89 of the inner cup section 70 and then rotating the body 98 so that the internally-threaded end 100 is threaded about the boss portion 89, the boss portion 89 is compressed against the ferrule 102 in a manner which urges the (leading) edges of the ferrule 102 inwardly against the outer surface of the tube 50. By threadably tightening the cylindrically-shaped body 96 far enough onto the boss portion 89, the ferrule 102 is compressed about the tube 50 so that the enclosure assembly 51 is fixed in position along the length of the tube 50.

It follows from the foregoing that as long as the cylindrically-shaped body 96 is not tightly threaded about the externally-threaded boss portion 89 of the inner cup section 70, the enclosure assembly 51, as well as the cylindrically-shaped body 96, is free to be slidably moved along the length of the tube 50. However, when it is desired that the enclosure assembly 51 be secured in a stationary condition along the length of the tube 50, the cylindrically-shaped body 96 is threadably tightened about the externally-threaded boss portion 89 of the inner cup section 70 so that the ferrule 102 is compressed about the tube 50.

Figure 5:
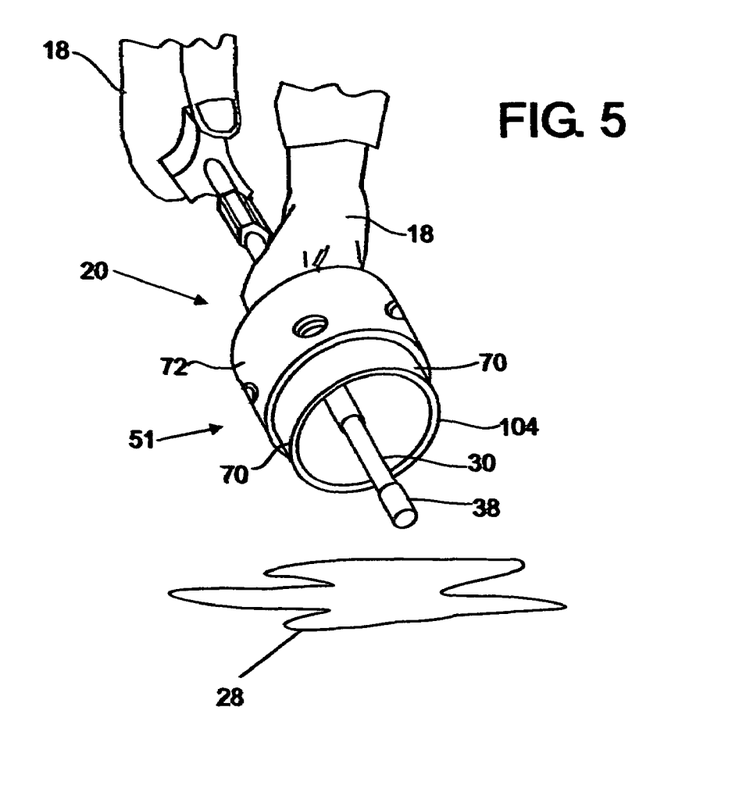
FIGS. 5 and 6 are views illustrating steps involved in using the FIG. 1 assembly.

To use the collection assembly 20 to transfer a sample amount of material to be identified or analyzed to the probe 24 (FIGS. 1 and 2) and with reference to FIG. 5, a collection tip 38 is slidably positioned upon the distal end 34 of the rod 30, and then the tube 50 and enclosure assembly 51 are slidably backed away from the distal end 34 of the rod 30 (i.e. moved toward the proximal end 32 of the rod 30) to position the collection tip 38 forwardly of the enclosure assembly 51 and, in particular, forwardly of the forward edge 104, of the inner cup section 70. The purpose served by backing the enclosure assembly 51 away from the distal end 34 is to prepare (or position) the collection tip 38 in a condition for contacting the material, indicated 28 in FIG. 5, to be sampled without interference from the enclosure assembly 51. Accordingly, the distance that the collection tip 38 should be positioned forwardly of the enclosure assembly 51 can be determined at the site of collection.

For example, if the material 28 to be sampled is contained within a drum, the collection tip 38 can be positioned forwardly of the enclosure assembly 51 by an appreciable amount or perhaps even attached to the end of an extension rod or rods to enable the material within the drum to be reached by the collection tip 38 through a bunghole of the drum. By comparison, if the material 28 to be sampled lay in a puddle upon the ground, the collection tip 38 can be positioned slightly forwardly of the enclosure assembly 51 to enable the collection tip 38 to be simply dipped into the material.

Figure 6:
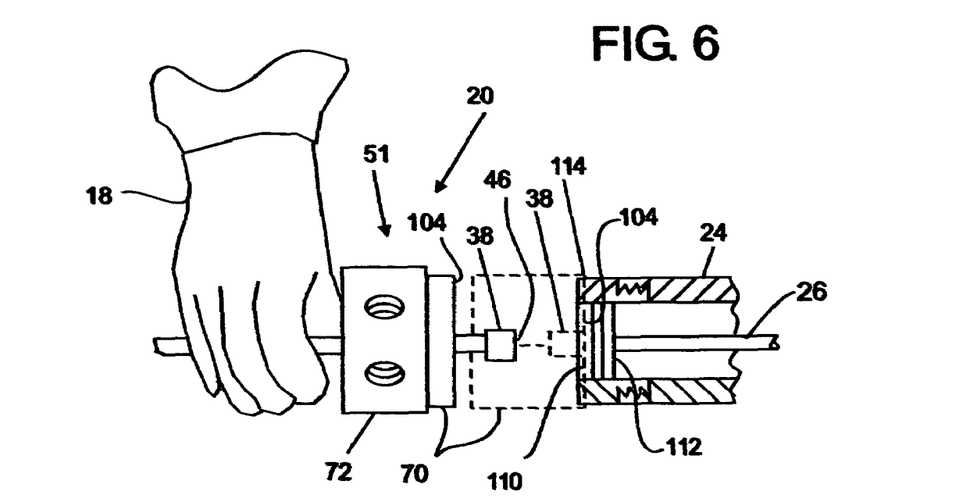

With the enclosure assembly 51 and tube 50 secured in a stationary position along the length of the tube 50 and rod 30, respectively, the collection tip 38 is then placed into contact with (e.g. dipped into) the material 28 to be sampled. When contacted by the collection tip 38, the material to be sampled is wicked into the porous material of the collection tip 38 (and more particularly, into the voids associated with the porous surface of the tip 38) and is thereby bound to the tip 38 until introduced to the mass spectrometer 22 (FIG. 1) by way of the probe 24 (FIGS. 1 and 6). In practice, the porous material of the collection tip 38 acts as a sponge to soak up an amount of sample when collecting the sample and thereafter slowly and evenly releases the sample when the sample is introduced to the mass spectrometer 22 for analysis.

With the sample 28 bound to the collection tip 38, the assembly 20 is then readied to transfer an amount of the sample 28 to the probe 24 (FIGS. 1 and 6) associated with the mass spectrometer 22 (FIG. 1) by re-adjusting the position of the closure assembly 51 with respect to the collection tip 38. In this connection and with reference to FIG. 6, the probe 24 is commonly comprised of a first layer 110 of metal (i.e. stainless steel) mesh and a second, or backing, layer 112 comprised of a synthetic membrane. Furthermore, each of the first and second layers 110, 112 is held in place upon the probe 24 by means of a retaining ring 114 which is threadably secured about the remainder of the probe 24, and it is around the annular exterior of the retaining ring 114 that the enclosure assembly 51 or, more specifically, the forward edges 104 of the inner cup section 70 is capable of being positioned when effecting the transfer of an amount of the sample 28 from the collection tip 38 to the probe 24. Accordingly and since the external diameter of the retaining ring 114 of conventional probes is normally about 2.375 inches, the outer diameter of the inner cup section 70 should preferably be no less than about 2.375 inches.

The transfer of an amount of the sample 28 collected upon the tip 38 is effected by placing the end portion 46 of the collection tip 38 adjacent the probe 24 while the enclosure assembly 51 is positioned about the external edges of the probe retaining ring 114. In this connection, the enclosure assembly 51 and tube 50 are adjusted in position relative to the collection tip 38 so that the end portion 46 of the collection tip 38 is either in contact with (i.e. touching) the first layer 110 of the probe 24 or is disposed in spaced relationship with (i.e. disposed rearwardly of) the first layer 110, depending upon the expected volatility of the material being sampled. In other words, when the forward edge 104 of the inner cup section 70 is positioned about the retaining ring 114, the collection tip 38 can be positioned in abutting relationship with (i.e. in contact with) the first layer 110 of the probe 24 (as is illustrated by the position of the tip 38 depicted in phantom in FIG. 6) or in spaced relationship with the first layer 110. In this latter-mentioned example, the collection tip 38 may, for example, be removed from the probe 24 by a distance which corresponds to the distance between the tip 38 as illustrated in solid lines in FIG. 6 and the first layer 110 of the probe 24.

With the tip 38 positioned an appropriate, or desired, distance from the probe 24, an amount of sample which is collected upon the tip 38 is vaporized by the internal heater of the probe 24 and drawn into the mass spectrometer 22 for characterization (e.g. for identification or analysis) for the material of the sample. It will be understood, however, that the sample of material which is collected upon the tip may be sufficiently volatile that it vaporizes at ambient temperature—in which case the heater of the probe 24 would only serve to diminish the signal.

During an operation involving the transfer of a vaporized amount of the collected sample from the collection tip 38 to the probe 24, the collection tip 38 is arranged in a desired positional relationship with the probe 24 in accordance with the expected volatility of the material being characterized. Generally speaking, the lower the volatility of the material being sampled, the closer to the probe 24 that the collection tip 38 should be positioned. Therefore, for low volatility materials, the collection tip 38 could be positioned in contact with the probe 24 (as is illustrated by the phantom-line position of the collection tip 38 of FIG. 6), and for materials which possess high volatility, the collection tip 38 can be positioned further from the probe 24 (e.g. wherein the spaced distance between the probe 24 and collection tip 38 is about 1.0 inches or further).

Along the lines of the foregoing, the outer tube 50 can be provided with a plurality of (e.g. three) annular rings with which the proximal end of the cylindrically-shaped body 96 can be selectively aligned for positioning the collection tip 38 in a desired positional relationship with respect to the forward edges 104 of the inner cup section 72 for transferring material samples from the tip 38 wherein the samples possess differing degrees (e.g. low, medium and high) of volatility.

Because the enclosure assembly 51 or, more specifically, the inner cup section 70 thereby surrounds the collection tip 38 as an amount of the collected sample is vaporized from the collection tip 38 and drawn into the probe 24, the inner cup section 70 helps to confine the vaporized sample to a region adjacent the probe 24 and helps to focus the vaporized sample upon the probe 24. Such a focusing of the vaporized sample by the cup section 70 is believed to ensure that neither too much nor too little of the sample is ultimately transferred from the collection tip 38 to the probe 24. Furthermore and by surrounding the collection tip 38 in this manner, the inner cup section 70 helps to increase the duration of the sample signal capable of being generated by the mass spectrometer 22, allowing a fuller characterization of the sample being analyzed or identified by the mass spectrometer 22.

The capacity of the vent openings 82 and 84 of the inner and outer cup sections 70 and 72 to be moved into and out of registry with one another provides alternative means by which the airspace disposed about the collection tip 38 or, more specifically, the interior of the inner cup section 70 can be vented during the transfer of an amount of vaporized sample from the collection tip 38 to the probe 24. For example, if the material of a collected sample is expected to be very volatile (i.e. possesses a high volatility), the inner and outer cup sections 70, 72 can be rotated to a position at which the vent openings 82, 84 are positioned in registry with one another (and thereby fully open the vent openings 82, 84) before movement of the forward edges 104 of the inner cup section 70 into contact with the probe 24. In contrast, if the material of a collected sample is expected to of low volatility, the inner and outer cup sections 70, 72 can be rotated to a position at which the vent openings 82, 84 are positioned out of registry with one another (to thereby close off the vent openings 82, 84) before movement of the forward edges 104 of the inner cup section 70 into contact with the probe 24.

Figure 7:
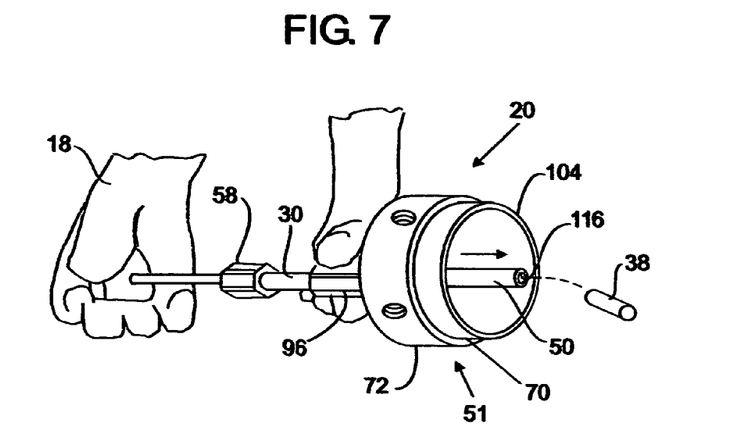
FIG. 7 is a perspective view illustrating how a used or contaminated collection tip is removed from the remainder of the assembly.

Upon completion of a sample-transferring operation, the collection assembly 20 is backed away from the probe 24, the cylindrically shaped body 58 is then loosened to permit the rod 30 to be slidably moved along the length of the tube 50. The cylindrically-shaped body 96 is also loosened to permit the tube 50 to be slidably moved through the boss portion 89. The tube 50 can then be forcibly urged forwardly toward and over the distal end 34 of the rod 30 (as illustrated in FIG. 7) so that the distal end, indicated 116 in FIGS. 4 and 7, of the tube 50 strikes and thereby forces the (used) collection tip 38 from the distal end 34 for disposal of the tip 38. The capacity of the assembly 20 to be used in such a manner to remove a used collection tip 38 from the distal end 34 of the rod 30 without the need that the tip 38 be touched or handled by the operator 18 is advantageous in this respect. Following the removal of a used collection tip 38 from the distal end 34 of the rod 30, a fresh, or unused, collection tip 38 can be installed upon the distal end 34 to prepare the assembly 20 for collecting another sample for analysis.

Figure 8:
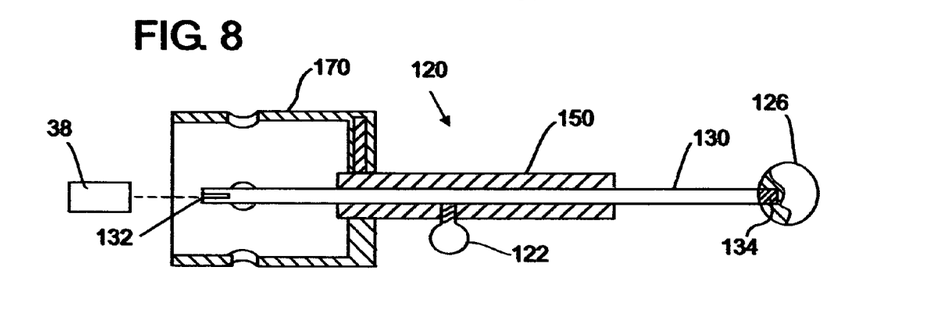
FIG. 8 is a perspective view of an alternative embodiment of an assembly within which features of the present invention are embodied.

It will be understood that numerous modifications and substitutions can be had to the aforedescribed embodiments without departing from the spirit of the invention. For example, although the aforedescribed embodiment of the assembly 20 has been shown and described as having a cup section 70 which is capable of being slidably moved along the length of an outer tube 50 between alternative positions, an assembly embodiment does not need to possess such a feature in accordance with the broader aspects of the invention. For example, there is illustrated in FIG. 8 an assembly 120 having an outer tube 150 which is positioned about an elongated rod 130 for sliding movement along the length thereof and a cap section 170 which is fixedly secured about the tube 150. The elongated rod 130 has a distal end 132 upon which a collection tip 38 can be slidably positioned and a proximal end 134 upon which a rounded knob 126 is threadably positioned. The tube 150 can be releasably secured along the length of the rod 130 by means of a thumb-tightenable set screw 122.

Furthermore and although the collection tip 38 of porous material has been shown and described as being cup-shaped in form having cylindrically-shaped walls 40 and a planar end portion 46, a collection tip in accordance with the broader aspects of the present invention can possess any of a number of alternative shapes. For example, rather than possess a planar end portion 46, a collection tip can possess more of a conical, or more-pointed end portion.

Figure 9:
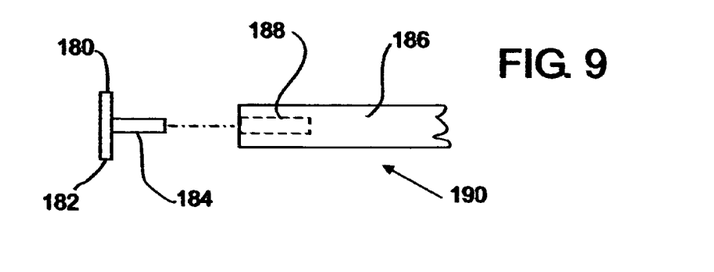
FIG. 9 is a fragmentary side elevational view of a collection tip and rod of another alternative embodiment of an assembly within which features of the present invention are embodied.

Further still, there is illustrated in FIG. 9 a collection tip 180 having a disc-shaped portion 182 for wicking, and thereby binding, an amount of material desired to be sampled and a post portion 184 joined centrally of the disc-shaped portion 182. The collection tip 180 is releasably joined to the distal end of a rod, indicated 186, of a collection assembly 190 by inserting the post portion 184 of the tip 180 into an axially-extending bore 188 formed in the distal end of the rod 186. It follows that unlike the collection tip 38 of FIGS. 1-8 whose cylindrically-shaped walls 40 cooperate with the external surfaces of a rod 30 for holding the tip 38 upon the rod 30, the collection tip 180 of FIG. 9 cooperates with the internal surfaces (of an axially-extending bore 188) of a rod 186 for holding the tip 180 upon the rod 186. Accordingly, the aforedescribed embodiments are intended for the purpose of illustration and not as limitation.

The invention claimed is:

1. An assembly for collecting a sample of a material desired to be characterized with diagnostic equipment including a probe through which an amount of the sample is introduced to the diagnostic equipment and wherein the sample of the material introduced to the probe is vaporized as it is introduced to the probe, the assembly comprising:

an elongated member having a proximal end with which the assembly is manipulated by a user, and a distal end;

a collection tip which is supported upon said distal end and which can be placed into contact with the material from which the sample is desired to be taken, the collection tip including a body of chemically-inert porous material for binding the sample of the material when the tip is placed into contact with the material from which the sample is desired to be taken for subsequent introduction of an amount of the bound sample through the probe of the diagnostic equipment;

an inner cup section which is connected to the elongated member so as to open axially therealong in a direction opposite the proximal end and which includes sidewalls which are positionable along the length of the elongated member and encircle the collection tip so that when the sample which is bound by the collection tip is ultimately introduced to the diagnostic equipment through the probe thereof in a vaporized condition, the inner cup section surrounds and helps to confine the vaporized sample to a region adjacent the probe, and wherein the inner cup section has an interior, and the sidewalls of the inner cup section define a plurality of vent openings which accommodate a venting of the interior of the inner cup section; and an outer cup section having sidewalls which are positioned about the inner cup section and which is connected to the inner cup section to accommodate movement of the outer cup section relative to the inner cup section between one condition and another condition, and the sidewalls of the outer cup section include a plurality of openings therearound so that by moving the outer cup section relative to the inner cup section between the one and the another conditions, the outer cup section is moved between a condition at which the sidewall openings of the outer cup section are disposed in registry with the vent openings of the inner cup section and another condition at which the vent openings of the inner cup section are completely covered by the sidewall of the outer cup section to thereby effect maximum vapor retention by the inner cup section.

2. The assembly as defined in claim 1, wherein the collection tip is adapted to cooperate with the distal end of the elongated member so that the tip is held by the elongated member and remains held by the elongated member during the course of the sample-collecting operation.

3. The assembly as defined in claim 1, wherein the collection tip is comprised of a material selected from a group of materials consisting of stainless steel and ceramics.

4. An assembly for collecting a sample of a material desired to be characterized with diagnostic equipment including a probe through which an amount of the sample is introduced to the diagnostic equipment and wherein the sample of the material introduced to the probe is vaporized as it is introduced to the probe, the assembly comprising:

an elongated member having a proximal end with which the assembly is manipulated by a user, and a distal end;

a collection tip which is supported upon said distal end and which can be placed into contact with the material from which the sample is desired to be taken, the collection tip including a body of chemically-inert porous material for binding the sample of the material when the tip is placed into contact with the material from which the sample is desired to be taken for subsequent introduction of an amount of the bound sample through the probe of the diagnostic equipment;

a cup section which is connected to the elongated member so as to open axially therealong in a direction opposite the proximal end and which includes sidewalls which are positionable along the length of the elongated member and encircle the collection tip so that when the sample which is bound by the collection tip is ultimately introduced to the diagnostic equipment through the probe thereof in a vaporized condition, the cup section surrounds and helps to confine the vaporized sample to a region adjacent the probe, and wherein the cup section is positioned upon the elongated member for sliding movement relative thereto and along the length thereof between a sample-collecting condition at which the collection tip is positioned forwardly of the cup section to facilitate the collection of a sample with the collection tip and a sample-transferring condition at which the collection tip is surrounded by the cup section; and means for releasably securing the cup section along the elongated member at each of the sample-collecting condition and the sample-transferring condition.

5. An assembly for collecting a sample of a material desired to be characterized with diagnostic equipment including a probe through which an amount of the sample is introduced to the diagnostic equipment and wherein the sample of the material introduced to the probe is vaporized as it is introduced to the probe, the assembly comprising:

an elongated member having a proximal end with which the assembly is manipulated by a user and a distal end;

a collection tip which is supported upon said distal end and which can be placed into contact with the material from which the sample is desired to be taken, the collection tip including a body of chemically-inert porous material for binding the sample of the material when the tip is placed into contact with the material from which the sample is desired to be taken for subsequent introduction of an amount of the bound sample through the probe of the diagnostic equipment;

a cup section which is connected to the elongated member so as to open axially therealong in a direction opposite the proximal end and which includes sidewalls which are positionable along the length of the elongated member and encircle the collection tip so that when the sample which is bound by the collection tip is ultimately introduced to the diagnostic equipment through the probe thereof in a vaporized condition, the cup section surrounds and helps to confine the vaporized sample to a region adjacent the probe, and wherein the cup section is positioned upon the elongated member for sliding movement relative thereto and along the length thereof between a sample-collecting condition at which the collection tip is positioned forwardly of the cup section to facilitate the collection of a sample with the collection tip and a sample-transferring condition at which the collection tip is surrounded by the cup section;

an elongated tube which is positioned about the elongated member for sliding movement relative thereto and along the length thereof, the cup section is positioned about the elongated tube for sliding movement relative to and along the length thereof;

means for releasably securing the elongated tube in a stationary position along the length of the elongated member; and means for releasably securing the cup section in a stationary position along the length of the elongated tube.

6. A collection assembly for collecting a sample of a material desired to be characterized by diagnostic equipment, such as a mass spectrometer, wherein there is associated with the diagnostic equipment a probe through which an amount of the collected sample is introduced to the diagnostic equipment from the assembly and wherein the sample of the material introduced into the probe with the collection assembly is vaporized as it is introduced to the probe, the collection assembly comprising:

an elongated rod having a proximal end with which the assembly is manipulated by a user, and an opposite distal end;

a collection tip which is supported by the opposite distal end of the rod for collecting a sample amount of the material desired to be characterized when the collection tip is placed into contact with the material, the collection tip being constructed of a chemically-inert porous material so that when the collection tip is placed into contact with the material, the collection tip wicks, and thereby binds, the sample amount of the material for subsequent introduction to the diagnostic equipment through the probe associated therewith;

an inner cup section which is connected to the elongated rod so as to open axially therealong in a direction opposite the proximal end and which includes sidewalls which are positionable along the length of the elongated rod so as to encircle the collection tip so that when the sample which is bound by the collection tip is ultimately introduced to the diagnostic equipment through the probe thereof in a vaporized condition, the inner cup section surrounds and helps to confine the vaporized sample to a region adjacent the probe and wherein the inner cup section has an interior, and the sidewalls of the inner cup section define a plurality of vent openings which accommodate a venting of the interior of the inner cup section; and an outer cup section having sidewalls which are positioned about the inner cup section and which is connected to the inner cup section to accommodate rotational movement of the outer cup section relative to the inner cup section between one condition and another condition, and the sidewalls of the outer cup section include a plurality of openings therearound so that by rotating the outer cup section relative to the inner cup section between the one and the another conditions, the outer cup section is rotated between a condition at which the sidewall openings of the outer cup section are disposed in registry with the vent openings of the inner cup section and another condition at which the vent openings of the inner cup section are completely covered by the sidewalls of the outer cup section, thereby effecting maximum vapor retention.

7. The assembly as defined in claim 6, wherein the collection tip is adapted to be slidably accepted by the opposite distal end of the rod and is adapted to remain held thereby during the course of the sample-collecting operation.

8. The assembly as defined in claim 7, wherein the collection tip is in the form of an open-ended cup which is positionable about the opposite distal end of the rod when the open end of the cup-shaped form of the collection tip is placed open-end first over the opposite distal end of the rod.

9. The assembly as defined in claim 8, wherein the end portion associated with the opposite distal end of the elongated rod defines a slit therealong which opens out of the opposite distal end thereof to facilitate the securement of the collection tip about the opposite distal end when the collection tip is positioned thereabout.

10. The assembly as defined in claim 6, wherein the inner cup section is positioned upon the elongated rod for sliding movement relative thereto and along the length thereof between a sample-collecting condition at which the collection tip is positioned forwardly of the inner cup section to facilitate the collection of the sample with the collection tip and a sample-transferring condition at which the collection tip is surrounded by the inner cup section, and the assembly further includes means for releasably securing the cup section along the elongated rod at each of the sample-collecting condition and the sample-transferring condition.

11. A collection assembly for collecting a sample of a material desired to be characterized by diagnostic equipment, such as a mass spectrometer, wherein there is associated with the diagnostic equipment a probe through which an amount of the collected sample is introduced to the diagnostic equipment from the assembly and wherein the sample of the material introduced into the probe with the collection assembly is vaporized as it is introduced to the probe, the collection assembly comprising:

an elongated rod having a proximal end with which the assembly is manipulated by a user and an opposite distal end;

a collection tip which is supported by the opposite distal end of the rod for collecting a sample amount of the material desired to be characterized when the collection tip is placed into contact with the material, the collection tip being constructed of a chemically-inert porous material so that when the collection tip is placed into contact with the material, the collection tip wicks, and thereby binds, the sample amount of the material for subsequent introduction to the diagnostic equipment through the probe associated therewith;

a cup section which is connected to the elongated rod so as to open axially therealong in a direction opposite the proximal end and which includes sidewalls which are positionable along the length of the elongated rod so as to encircle the collection tip so that when a sample which is bound by the collection tip is ultimately introduced to the diagnostic equipment through the probe thereof in a vaporized condition, the cup section surrounds and helps to confine the vaporized sample to a region adjacent the probe, and wherein the cup section is positioned upon the elongated rod for sliding movement relative thereto and along the length thereof between a sample-collecting condition at which the collection tip is positioned forwardly of the cup section to facilitate the collection of the sample with the collection tip and a sample-transferring condition at which the collection tip is surrounded by the cup section;

means for releasably securing the cup section along the elongated rod at each of the sample-collecting condition and the sample-transferring condition;

an elongated tube which is positioned about the elongated rod for sliding movement relative thereto and along the length thereof, the cup section is positioned about the elongated tube for sliding movement relative to and along the length thereof;

means for releasably securing the elongated tube in a stationary position along the length of the elongated rod; and means for releasably securing the cup section in a stationary position along the length of the elongated tube.

12. A method for transferring a sample of a material desired to be characterized with diagnostic equipment having a probe through which an amount of the sample is introduced to the diagnostic equipment, and wherein the sample of material is vaporized as it is introduced to the probe, the method comprising the steps of:

providing an assembly including:

(a) an elongated member having a proximal end with which the assembly is manipulated by a user, and a distal end;

(b) a collection tip which is supported upon said distal end and which can be placed into contact with the material from which the sample is desired to be taken, the collection tip including a body of chemically-inert porous material for binding the sample of material when the tip is placed into contact with the material for binding a sample of material when the tip is placed into contact with the material from which a sample is desired to be taken for subsequent introduction of an amount of the bound sample through the probe of the diagnostic equipment; and (c) a cup section which is connected to the elongated member so as to open axially therealong in a direction opposite the proximal end and which includes sidewalls which are positionable along the length of the elongated member and encircle the collection tip so that when a sample which is bound by the collection tip is ultimately introduced to the diagnostic equipment through the probe thereof in a vaporized condition, the cup section surrounds and helps to confine the vaporized sample to a region adjacent the probe, and wherein the cup section is positioned upon the elongated member for sliding movement relative thereto and along the length thereof between a sample-collecting condition at which the collection tip is positioned forwardly of the cup section to facilitate the collection of the sample with the collection tip and a sample-transferring condition at which the collection tip is surrounded by the cup section;

(d) means for releasably securing the cup section along the elongated member at each of the sample-collecting condition and the sample-transferring condition;

positioning the cup section along the elongated member in the sample-collecting condition;

placing the collection tip into contact with the material desired to be characterized so that the collection tip wicks, and thereby binds, the sample of the material;

withdrawing the collection tip from the material and positioning the cup section along the elongated member in the sample-transferring condition and then placing the collection tip adjacent the probe of the diagnostic equipment for introduction of an amount of the bound sample to the diagnostic equipment and so that while the collection tip is positioned adjacent the probe during this step, the collection tip is surrounded by the cup section.

* * * * *